(12) United States Patent
Swinney et al.

(10) Patent No.: US 10,485,626 B2
(45) Date of Patent: Nov. 26, 2019

(54) TRANSPORTATION OF MEDICAL INSTRUMENTS

(71) Applicant: TRISTEL PLC, Snailwell Cambridgeshire (GB)

(72) Inventors: Paul Swinney, Snailwell (GB); Julija Shabanova, Cambridge (GB); Esther Jansen, Cambridge (GB)

(73) Assignee: TRISTEL PLC, Snailwell Cambridgeshire (GB)

( * ) Notice: Subject to any disclaimer, the term of this patent is extended or adjusted under 35 U.S.C. 154(b) by 48 days.

(21) Appl. No.: 15/938,640

(22) Filed: Mar. 28, 2018

(65) Prior Publication Data

US 2018/0214232 A1 Aug. 2, 2018

Related U.S. Application Data

(63) Continuation-in-part of application No. 15/129,692, filed as application No. PCT/GB2015/051440 on May 15, 2015, now abandoned.

(30) Foreign Application Priority Data

May 20, 2014 (GB) .................................. 1408955.1

(51) Int. Cl.
*A61B 50/31* (2016.01)
*A61B 50/36* (2016.01)
(Continued)

(52) U.S. Cl.
CPC .......... *A61B 50/31* (2016.02); *A61B 1/00144* (2013.01); *A61B 50/36* (2016.02);
(Continued)

(58) Field of Classification Search
USPC ............ 206/459.5, 807, 363, 364; 383/210.1
See application file for complete search history.

(56) References Cited

U.S. PATENT DOCUMENTS

| RE30,958 E | 6/1982 | White |
| 4,348,440 A | 9/1982 | Kriozere |

(Continued)

FOREIGN PATENT DOCUMENTS

| DE | 202004008867 U1 | 10/2004 |
| DE | 202007001713 U1 | 7/2007 |

(Continued)

*Primary Examiner* — Jacob K Ackun
(74) *Attorney, Agent, or Firm* — Hayes Soloway PC

(57) ABSTRACT

The present disclosure provides a system to transport medical instruments. The system includes an instrument bag configured to receive a medical instrument. The instrument bag forms an opening. A subjacent label is at least partially disposed along a peripheral surface of the opening of the instrument bag. The subjacent label includes a first portion engaged to an exterior surface of the instrument bag, and a second portion configured to be removably engaged to the instrument bag. A superjacent label is at least partially disposed along a peripheral surface of the opening of the instrument bag. The superjacent label includes an attached portion removably adhered to the subjacent label, and a free portion configured to be removably engaged to at least one of subjacent label and the instrument bag.

20 Claims, 10 Drawing Sheets

(51) Int. Cl.
  *A61B 90/94*    (2016.01)
  *B65D 33/00*    (2006.01)
  *A61B 1/00*     (2006.01)
  *A61B 50/30*        (2016.01)
  *A61B 50/00*        (2016.01)

(52) U.S. Cl.
  CPC ............ *A61B 90/94* (2016.02); *B65D 33/004* (2013.01); *A61B 2050/002* (2016.02); *A61B 2050/314* (2016.02)

(56) References Cited

U.S. PATENT DOCUMENTS

| | | |
|---|---|---|
| 4,402,453 A | 9/1983 | Regenstein, Jr. |
| 4,510,621 A | 4/1985 | Sak |
| 4,785,940 A | 11/1988 | Wilson |
| 4,874,090 A | 10/1989 | Dyke |
| 4,980,222 A | 12/1990 | Rivera et al. |
| 5,222,600 A | 6/1993 | Stoddard |
| 5,366,087 A | 11/1994 | Bane |
| 5,643,188 A | 7/1997 | Oliveira |
| 5,692,834 A | 12/1997 | Pagano |
| 5,824,380 A | 10/1998 | Hagen |
| 6,113,271 A | 9/2000 | Scott |
| 6,234,310 B1 | 5/2001 | Goldhaber |
| 6,428,867 B1 | 8/2002 | Scott et al. |
| 7,306,263 B2 | 12/2007 | Hudson |
| 2003/0188981 A1 | 10/2003 | Sedley |
| 2004/0178099 A1 | 9/2004 | Natay-Curley |
| 2004/0264813 A1 | 12/2004 | Steffens |
| 2006/0207144 A1* | 9/2006 | Milliorn ............ G09F 3/10 40/637 |
| 2006/0251342 A1* | 11/2006 | Forman ............ B65D 33/1691 383/62 |
| 2008/0013869 A1* | 1/2008 | Forman ............ B65D 33/1691 383/210 |
| 2010/0223823 A1* | 9/2010 | Gordon ............ G09F 3/0289 40/316 |
| 2011/0233079 A1 | 9/2011 | Macinnes et al. |
| 2012/0294553 A1 | 11/2012 | Chang |
| 2014/0133785 A1* | 5/2014 | Diviesti ............ A61F 13/0008 383/210.1 |
| 2014/0294322 A1* | 10/2014 | Truslow ............ B65D 33/18 383/6 |

FOREIGN PATENT DOCUMENTS

| | | |
|---|---|---|
| EP | 0134130 A2 | 3/1985 |
| EP | 0515086 A1 | 11/1992 |
| GB | 1482523 | 8/1977 |
| GB | 2243143 A | 10/1991 |
| GB | 2526313 A | 11/2015 |
| WO | 03/034936 A1 | 5/2003 |
| WO | 2005/027767 A1 | 3/2005 |
| WO | 2005/107823 A1 | 11/2005 |
| WO | 2011070329 A1 | 6/2011 |

* cited by examiner

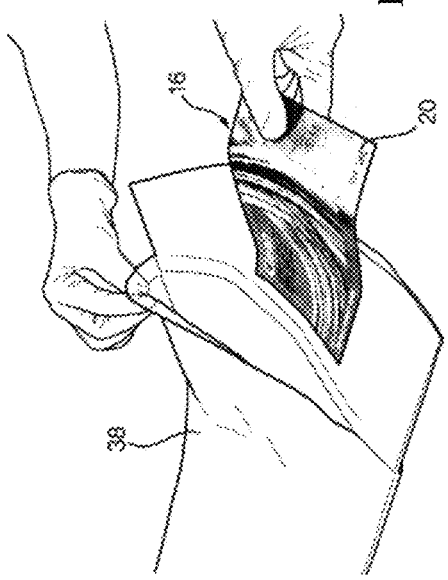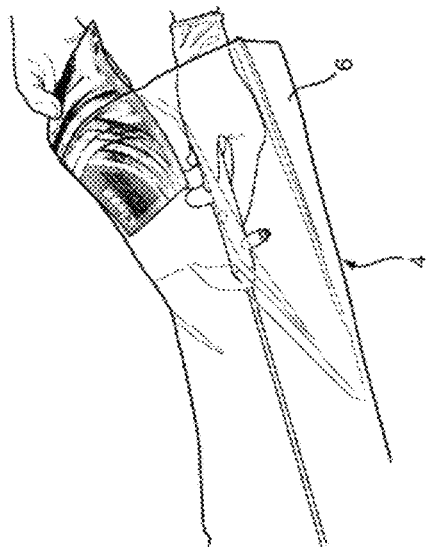

TRANSPORTATION OF MEDICAL INSTRUMENTS

CROSS REFERENCE TO RELATED APPLICATIONS

This application is a continuation-in-part of co-pending U.S. patent application Ser. No. 15/129,692, filed Sep. 27, 2016, which itself is a 371 of International Application Serial No. PCT/GB2015/051440, filed May 15, 2015, which claims priority of United Kingdom Patent Application No. 1408955.1, filed May 20, 2014, each of which this application claims benefit from and the contents of which are hereby incorporated by reference.

FIELD OF THE INVENTION

The present disclosure relates to a system for the transportation and storage of medical instruments.

BACKGROUND TO THE INVENTION

Medical devices, such as endoscopes, are used for the internal examination of the human or animal body. They are produced in a range of lengths and diameters depending on the intended use. Typically, an endoscope is flexible, and may have an internal channel, or lumen, down which fluids may be directed. Because of the invasive nature of endoscopy, it generally is necessary that an endoscope be thoroughly cleaned and disinfected after use on a patient before it is used for another procedure. After use, the endoscope undergoes a decontamination procedure involving cleaning, disinfecting and sterilising prior to re-use. Conventional decontamination systems generally provide cleaning wipes to remove organic deposits, disinfectant/sterilising wipes, and sterile rinse wipes to remove disinfectant residues. Each wipe is typically provided in its own sealed sachet which may provide information such as lot or batch number, date of manufacture and expiry date. This information may be transferred to a record book as part of an audit trail to provide a record that an instrument has been properly decontaminated and the date on which this was done.

Each sachet may also optionally be provided with a data carrier such as a bar code or RFID tag, and corresponding data carriers may be provided for the instrument to be decontaminated and for patient and operator details. When carrying out a decontamination procedure, each data carrier is read and a print-out may be produced which provides confirmation that the decontamination procedure has been carried out in accordance with correct procedure, and optionally details such as the instrument decontaminated, the operator, and data specific to a patient. These systems facilitate the provision of proper audit trails to ensure that an instrument is known to have been decontaminated in accordance with procedure.

Ideally, the decontamination procedure is carried out in close proximity to where the endoscope will be used, and preferably immediately before it is to be used. However, such ideal conditions seldom occur. Typically, a decontaminated instrument must be temporarily stored until required, and it may need to be used in a procedure room which is some distance from where decontamination took place.

Some conventional systems use a re-usable tray having an endoscope compartment, a single-use disposable tray-liner having an open-faced pouch, and a pouch-closing protective cover. The tray-liner is impermeable to body fluids, and flexible enough that the pouch is able to conform to the contours of the endoscope compartment. When an endoscope is placed in the pouch within the endoscope compartment, the protective cover can be detachably extended across the open face of the pouch from one edge to another so as to enclose and protect the endoscope.

To provide traceability data, an operator may place a ticket carrying the data in the tray, under the tray-liner. A problem with this is that it is necessary to remove the protective cover and the tray-liner to access the traceability data. Movements in the course of this operation generate particles and increase the risk of contamination. An alternative, in which a ticket is placed on the instrument itself, also introduces an undesirable source of potential contamination.

Another transportation system provides two large instrument bags: one for decontaminated endoscopes and the other for contaminated endoscopes. The two bags may be of different colours to allow easy differentiation. However, the action of unfolding the bags is also liable to generate potentially contaminating particles.

SUMMARY OF THE INVENTION

The present disclosure generally relates to a system to transport a medical instrument. The system includes an instrument bag configured to receive a medical instrument. The instrument bag forms an opening. The system includes a subjacent label at least partially disposed along a peripheral surface of the opening of the instrument bag. The subjacent label includes a first portion engaged to an exterior surface of the instrument bag and a second portion configured to be removably engaged to the instrument bag. The system includes a superjacent label at least partially disposed along a peripheral surface of the opening of the instrument bag. The superjacent label includes an attached portion removably adhered to one of the subjacent label and the exterior surface of the instrument bag, and a free portion configured to be removably engaged to the instrument bag.

In some embodiments, the free portion of the superjacent label may comprise a removable adhesive cover configured to expose an adhesive when the removable adhesive cover is removed. The free portion of the superjacent label may be adhered to an opposing side of the instrument bag to close the opening of the instrument bag.

In some embodiments, the removable adhesive cover may be substantially L-shaped. The superjacent label may be removed from the subjacent label and the instrument bag. The second portion of the subjacent label may comprise a second removable adhesive cover configured to expose a second adhesive when the second removable adhesive cover is removed.

In some embodiments, the second portion of the subjacent label may be adhered to an opposing side of the instrument bag to close the opening of the instrument bag. The superjacent label may be disposed over the subjacent label. A length of the superjacent label may be greater than a length of the subjacent label. The superjacent label may form a pocket disposed between the attached portion of the superjacent label and the adhered part of the free portion In some embodiments, a data carrier may be disposed within the pocket. The data carrier may comprise a disinfectant material and includes information relating to the medical instrument.

In some embodiments, the superjacent label indicates that the medical instrument is clean, and the subjacent label indicates that the medical instrument is contaminated. The system may include an outer bag, wherein the instrument bag is disposed within the outer bag. The system may include a box, wherein one or more instrument bags are disposed within the box for sterile transport. The instrument bag may include a fluid-impervious material and is configured to be sealed to prevent ingress of contaminants.

A method includes disposing a subjacent label at least partially along a peripheral surface of an opening of an instrument bag. The subjacent label includes a first portion engaged to an exterior surface of the instrument bag and a second portion configured to be removably engaged to the instrument bag. The method also includes disposing a superjacent label at least partially along the peripheral surface of the opening of the instrument bag. The superjacent label includes an attached portion removably adhered to at least one of the subjacent label and the exterior surface of the instrument bag and a free portion configured to be removably engaged to the instrument bag The method may include removing a removable adhesive cover disposed on the free portion of the superjacent label to expose an adhesive, and adhering the free portion of the superjacent label to an opposing side of the instrument bag to close the opening of the instrument bag.

The method may include removing the attached portion of the superjacent label from at least one of the subjacent label and the exterior surface of the instrument bag.

The method may include removing a subjacent label removable adhesive cover disposed on the second portion of the subjacent label to expose a second adhesive, and adhering the second portion of the subjacent label to the opposing side of the instrument bag to close the opening of the instrument bag

BRIEF DESCRIPTION OF THE DRAWINGS

The present disclosure will now be further described, by way of example, with reference to the following drawings in which:

FIGS. 4-12 illustrate stages in the use of system in accordance with some embodiments of the present disclosure.

Figure 1A:
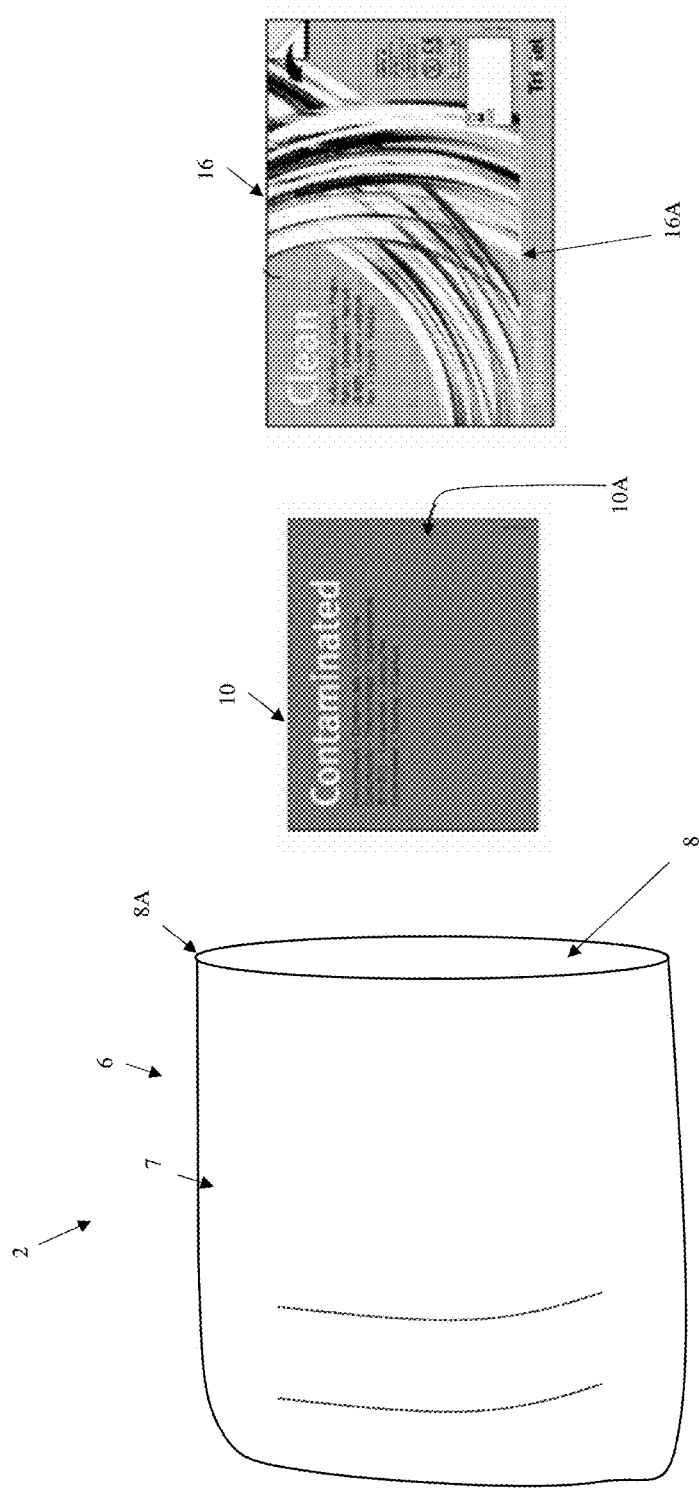
FIG. 1A is a front-facing exploded view of the system, in accordance with some embodiments of the present disclosure.

These and other features of the present embodiments will be understood better by reading the following detailed description, taken together with the figures herein described. In the drawings, each identical or nearly identical component that is illustrated in various figures may be represented by a like numeral. For purposes of clarity, not every component may be labelled in every drawing. Furthermore, as will be appreciated in light of this disclosure, the accompanying drawings are not intended to be drawn to scale or to limit the described embodiments to the specific configurations shown.

DETAILED DESCRIPTION

The present disclosure generally relates to a system for providing storage of a medical instrument. An instrument bag may be configured to receive and transport a medical instrument. The instrument bag may form an opening for receiving a medical instrument.

A superjacent label may be disposed over a subjacent label. An attached portion of the superjacent label may be disposed on at least one of the subjacent label and an exterior surface of the instrument bag. A free portion of the superjacent label may be free and not engaged to the instrument bag. The free portion may include a first removable adhesive cover that, when removed, exposes an adhesive that may be adhered to the instrument bag and close the opening of the instrument bag.

The subjacent label may be disposed on an exterior surface of the instrument bag. The subjacent label may be partially disposed on the exterior surface of the bag, and a portion of the subjacent label may be disposed along the peripheral surface of the opening. A first portion of the subjacent label may be engaged to the exterior surface of the instrument bag. A second portion of the subjacent label may be free and not engaged to the instrument bag. The subjacent label may include a subjacent label adhesive cover that, when removed, exposes a second adhesive that may be adhered to an opposing side of the instrument bag to close the opening.

FIG. 1A is a front-facing exploded view of the system 2, in accordance with some embodiments of the present disclosure. As shown in FIG. 1A, the system 2 includes an instrument bag 6. The instrument bag 6 may include a plastic material known in the medical industry to maintain a sterile environment and prevent the permeation of pathogens. The instrument bag 6 may include a size suitable to receive an appropriate medical instrument. In some embodiments, the instrument bag 6 forms an opening 8. The opening 8 may allow for a medical instrument to be received and/or removed from the instrument bag 6.

As depicted in FIG. 1A, the system 2 may include superjacent label 16. In an embodiment, the superjacent label 16 is superimposed over the subjacent label 10, which can be seen in FIG. 3. The superjacent label 16 may include a front face 16A. The front face 16A may be the face of the superjacent label 16 facing opposite the instrument bag 6. The superjacent label 16 may be at least partially disposed along a peripheral surface 8A of the opening 8.

The system 2 may include a subjacent label 10. In an embodiment, the subjacent label 10 may be disposed between the exterior surface 7 of the instrument bag 6 and the superjacent label 16. The subjacent label 10 may include a front face 10A.

Figure 1B:
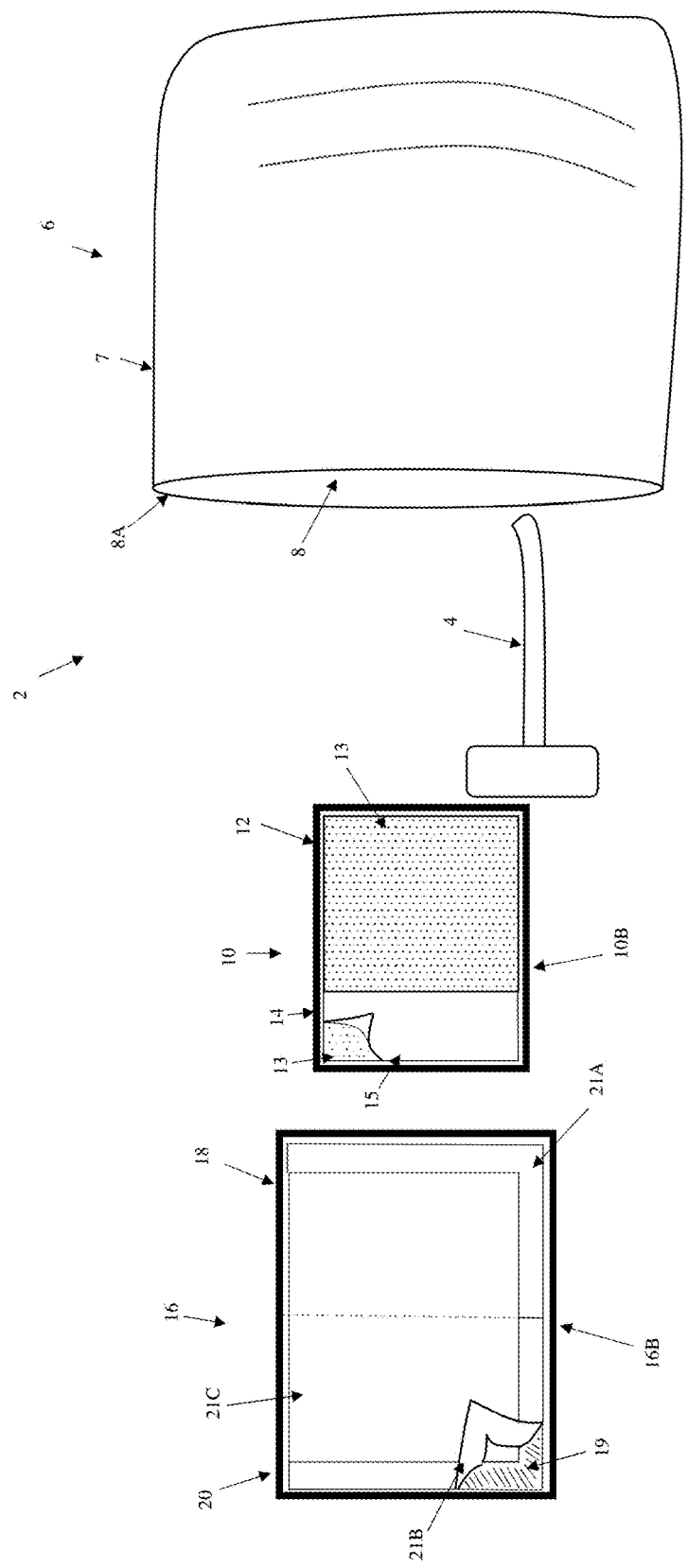
FIG. 1B is a rear-facing exploded view of the system, in accordance with some embodiments of the present disclosure.

FIG. 1B is a rear-facing exploded view of the system, in accordance with some embodiments of the present disclosure. The embodiment as shown in FIG. 1B illustrates the back face 10B of the subjacent label 10 and the back face 16B of the superjacent label 16. The back face of the subjacent label 10 and the superjacent label 16B may include the face of the label that is configured to face the instrument bag 6.

As shown in FIG. 1B, the superjacent label 16 may include an attached portion 18. The attached portion 18 may include the portion of the superjacent label disposed to at least one of the subjacent label 10 and the exterior surface 7 of the instrument bag 6. The superjacent label 16 may be at least partially disposed along a peripheral surface 8A of the opening 8.

As shown in FIG. 1B, the attached portion 18 of the superjacent label 16 may include an adhesive 19. The adhesive 19 may be disposed on the back face 10B of the superjacent label 16. In an embodiment, adhesive 19 may be applied to the entire back face 16B of the superjacent label 16. The superjacent label 16 may include a first removable adhesive cover 21A. The first removable adhesive cover 21A may be disposed within the attached portion 18. The first removable adhesive cover 21A may be removed to expose the adhesive 19 and adhere the attached portion 18 to at least one of the subjacent label 10 and the instrument bag 6. The first removable adhesive cover 21A may be substantially L-shaped. The adhesive 19 may include any known adhesive in the industry suitable to removably engage the superjacent label 16 to another component, such as the instrument bag 6.

As shown in FIG. 1B, the superjacent label 16 may include a free portion 20. In some embodiments, the free portion 20 of the superjacent label 16 may not be engaged to the exterior surface 7 of the instrument bag 6. In some embodiments, the free portion 20 of the superjacent label 16 may include a second removable adhesive cover 21B. The second removable adhesive cover 21B may be disposed on the back face 16B of the superjacent label 16. In some embodiments, the second removable adhesive cover 21B is substantially L-shaped. The second removable adhesive cover 21B may also be substantially square, rectangular, or another suitable configuration.

As shown in FIG. 1B, the second removable adhesive cover 21B may be removed and/or peeled from the superjacent label 16. When the second removable adhesive cover 21B is removed, a portion of the adhesive 19 may be exposed. When the adhesive 19 is exposed, the free portion 20 of the superjacent label 16 may adhere to another component. In some embodiments, the free portion 20 of the superjacent label 16 may adhere to the opposing side of the instrument bag 6, which may close the opening 8.

The back face 16B may include a third removable adhesive cover 21C. The third removable adhesive cover 21C may be disposed over the remaining portion of the back face 16B.

As shown in FIG. 1B, the subjacent label 10 may include a first portion 12. The first portion 12 may be engaged to the exterior surface 7 of the instrument bag 6. A second adhesive 13 may removably adhere the subjacent label 10 to the exterior surface 7 of the instrument bag 6. The second adhesive 13 may include a suitable adhesive known in the industry.

The subjacent label 10 may include a second portion 14. In some embodiments, the second portion 14 of the subjacent label 10 may not be engaged to the exterior surface 7 of the instrument bag 6. As shown in FIG. 1B, the second portion 14 of the subjacent label 10 may include subjacent label adhesive cover 15. The subjacent label adhesive cover 15 may be disposed on the back face 10B of the subjacent label 10. The subjacent label adhesive cover 15 may be removed and expose a portion of the second adhesive 13. The second adhesive 12 exposed may adhere the second portion 14 to an opposing side of the instrument bag 6 to close the opening 8.

The system 2 may include a medical instrument 4. The medical instrument 4 may comprise any known medical instrument, such as an endoscope, for example. The medical instrument 4 may be removably placed within the instrument bag 6.

Figure 2A:
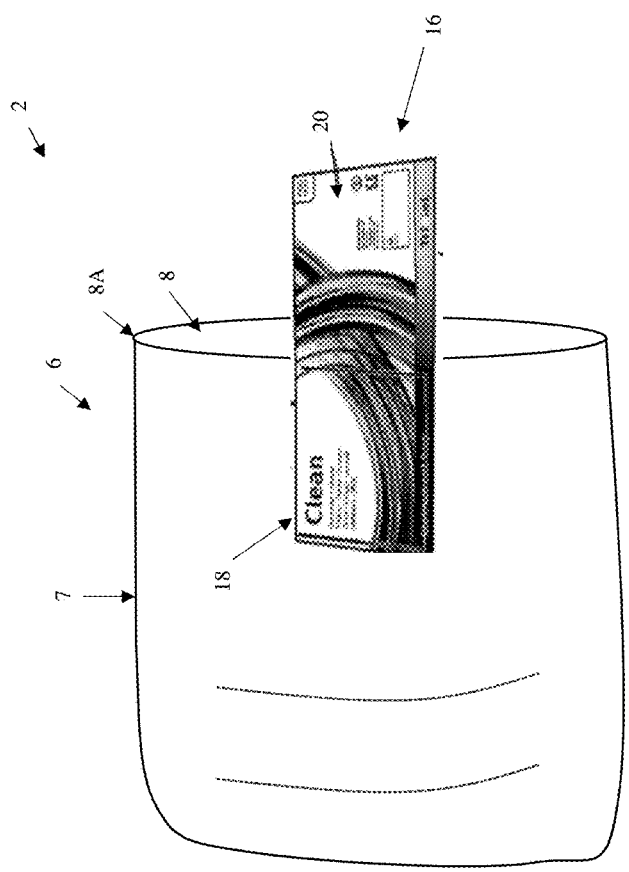
FIGS. 2A-2B illustrate perspective views of the system, in accordance with some embodiments of the present disclosure.
Figure 2B:
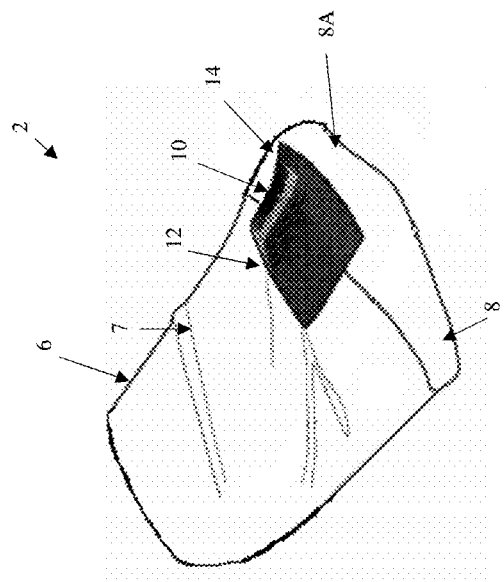

FIGS. 2A-2B illustrate perspective views of a system 2, in accordance with some embodiments of the present disclosure. As shown in FIG. 2A, the superjacent label 16 may include an attached portion 18 and a free portion 20. The attached portion 18 may be disposed on an exterior surface 7 of the instrument bag 6. The attached portion 18 may be at least partially disposed along the peripheral surface 8A of the opening 8. The free portion 20 may be free and not engaged to the instrument bag 6.

As shown in FIG. 2B, the subjacent label 10 may be at least partially disposed on the exterior surface 7 of the instrument bag 6. The first portion 12 of the subjacent label 10 may be at least partially disposed along a peripheral surface 8A of the opening 8. The second portion 14 of the subjacent label 10 may be free and not engaged to the instrument bag 6.

Figure 3:
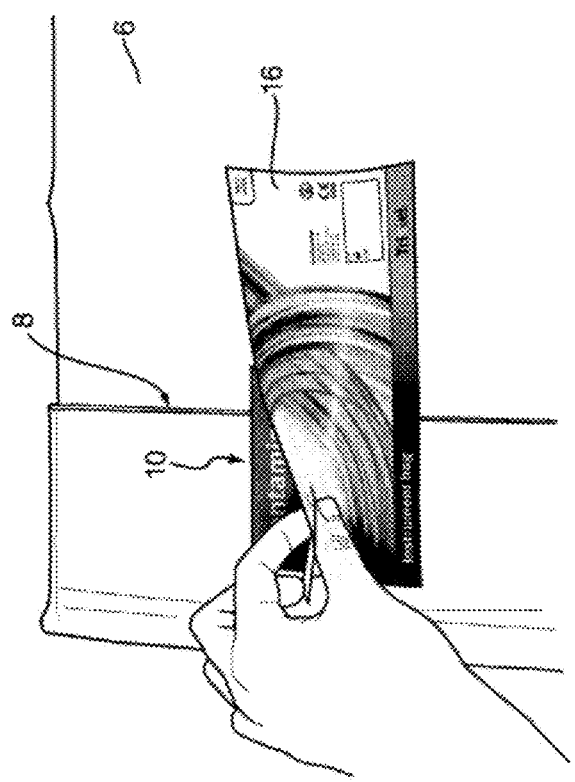
FIG. 3 illustrates a perspective view of the system including the superjacent label and the subjacent label, in accordance with some embodiments of the present disclosure.

FIG. 3 illustrates a schematic view of the system 2, in accordance with some embodiments of the present disclosure. As shown in FIG. 3, the superjacent label 16 is disposed over the subjacent label 10. The subjacent label 10 may be disposed between the instrument bag 6 and the superjacent label 16. In some embodiments, the superjacent label 16 includes a greater length and a greater width than that of the subjacent label 10. The superjacent label 16 may be removably engaged to the subjacent label 10 via the adhesive 19.

FIGS. 4-12 illustrate stages in the use of system in accordance with some embodiments of the present disclosure. FIGS. 6-14 are for illustrative purposes only, and the present system may be implemented in any suitable order or method.

Figure 4:
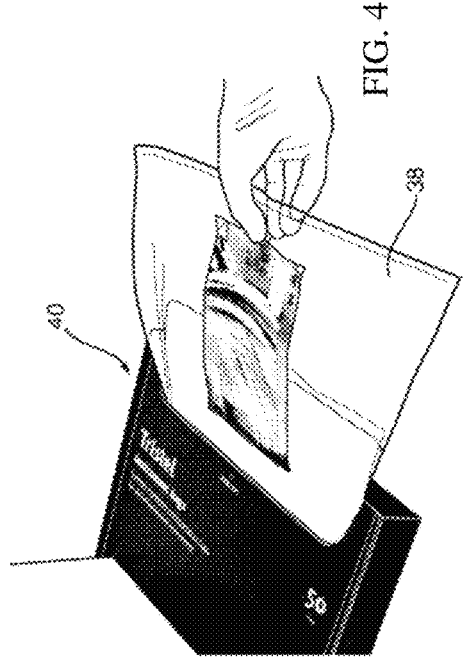

As shown in FIG. 4, one or more instrument bags 6 may be disposed within box 40. Each instrument bag 6 may be disposed within an outer bag 38. The outer bag 38 may be formed of a fluid-impervious material and is sealed to prevent ingress of contaminants, which may provide additional sterility of the instrument bag 6. In an embodiment, the instrument bag 6 may be sterilized using a suitable method, such as gamma-irradiation, for example. The instrument bag 6 may be sterilized prior to or after the instrument bag 6 is disposed within the outer bag 38.

The instrument bags 6 may be placed into box 40. Sterilisation may be carried out by gamma-irradiation on the instrument bags 6 when packed in the box 40. One or more instrument bags 6 may be transported using the box 40. To access an instrument bag 6, an outer bag 38 may be removed from the box 40.

Figure 5:
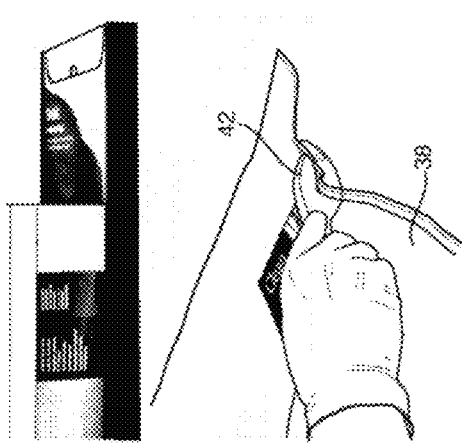

As shown in FIG. 5, to access the instrument bag 6, the outer bag 38 may be cut along an edge of the outer bag 38 to expose the instrument bag. The outer bag 38 may be cut using a suitable cutting instrument 42. In some embodiments, the outer bag 38 is omitted. In these embodiments, an instrument bag 6 may be removed from the box 40 by pulling on the superjacent label 16.

In FIG. 6, an instrument bag 6 may be removed from the outer bag 38. An instrument bag 6 may be removed from the outer bag 38 by pulling the free portion 20 of the superjacent label 16.

As shown in FIG. 7, a medical instrument 4 may be disposed within the instrument bag 6. To maintain a sterile environment, the free portion 20 of the superjacent label 16 may be held to allow the medical instrument 4 to be placed through the opening 8 of the instrument bag 6. The interior of the instrument bag 6 may comprise a sterile environment as to prevent contamination of the medical instrument 4.

Figure 8:
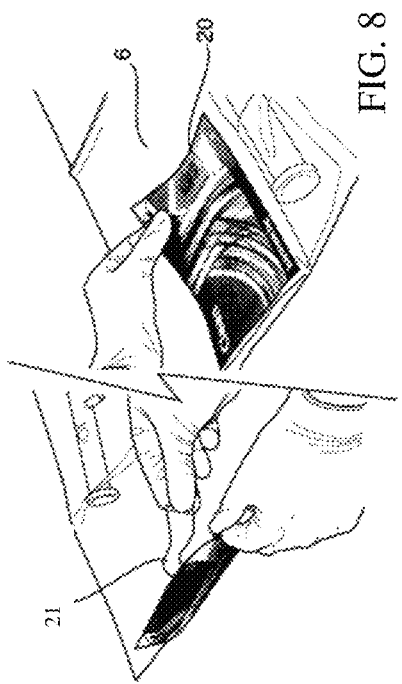

As shown in FIG. 8, the second removable adhesive cover 21B of the superjacent label 16 may be removed, exposing the second adhesive. The free portion 20 of the superjacent label 16 may be adhered to the instrument bag 6. The adhesive 19 may adhere the superjacent label 16 to the exterior surface 7 of the instrument bag 6. In an embodiment, the free portion 20 of the superjacent label 16 may be disposed on the instrument bag 6 to close the opening 8.

Figure 9:
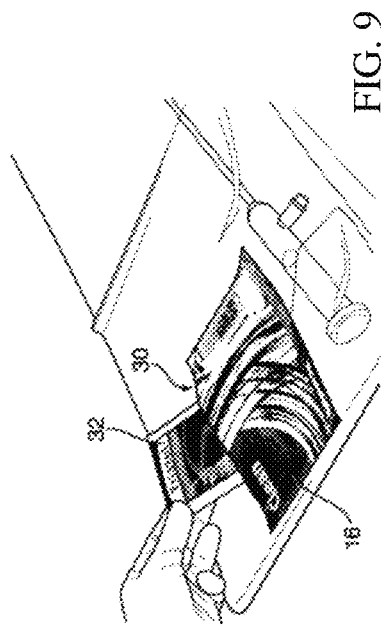

As shown in FIG. 9, the superjacent label 16 may form a pocket 30. In an embodiment, a portion of the superjacent label 16 is not adhered to the instrument bag 6. The third removable adhesive cover 21C may not be removed in some embodiments, where the portion of the back face 16B not adhered to the instrument bag 6 forms the pocket. The pocket 30 may be formed between the superjacent label 16 and the instrument bag 6.

As shown in FIG. 9, a data carrier 32 may be disposed within the pocket 30. In an embodiment, the data carrier 32 may comprise a sachet of the sporicidal wipe used to disinfect the medical instrument 4. In another embodiment, the data carrier 32 may comprise information including, but not limited to, patient notes, instrument records, lot or batch number of the disinfectant used on the instrument, or use-by date of the disinfectant.

Figure 10:
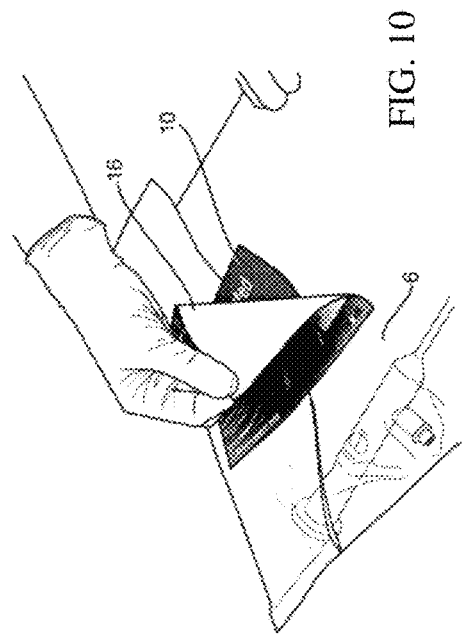

As shown in FIG. 10, the superjacent label 16 may be removed. The superjacent label 16 may be removed when it is appropriate to remove the clean medical instrument 4 from the instrument bag 6. In some embodiments, the data carrier 32 may be removed from the pocket 30. The superjacent label 16 may be removed from the instrument bag 6 by applying an opposing force to disengage the adhesives engaging the instrument bag 6 and the superjacent label 16.

Figure 11:
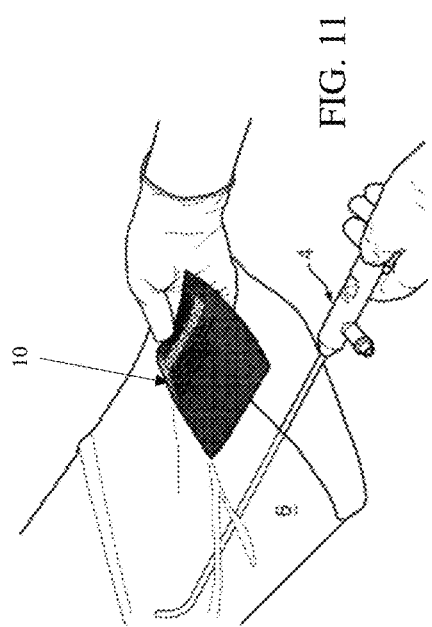

As shown in FIG. 11, if the superjacent label 16 is removed, the medical instrument 4 may be removed from the opening 8.

Figure 12:
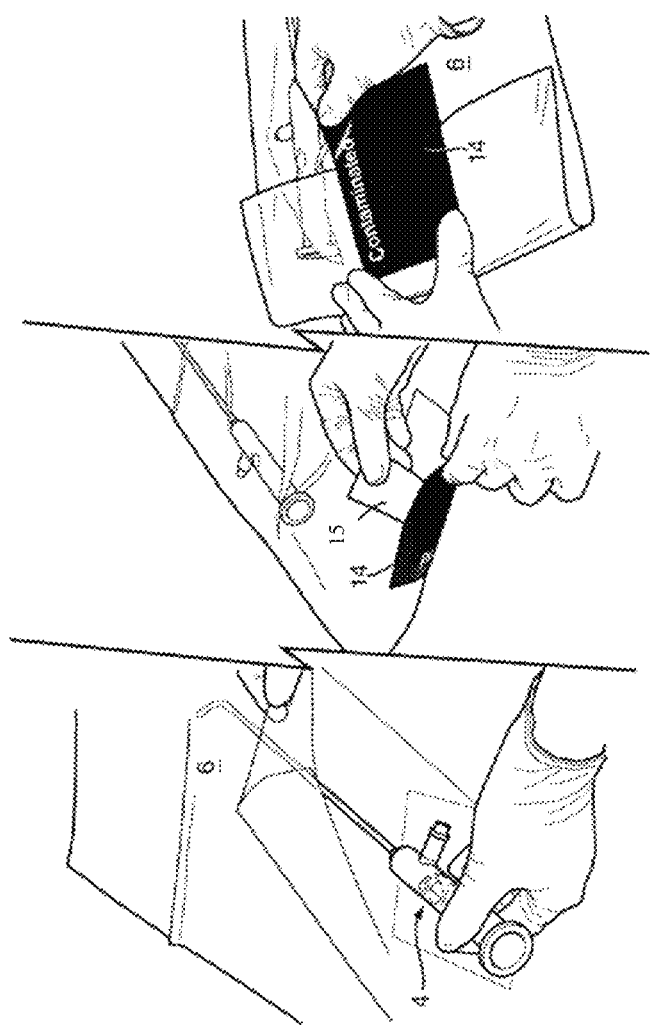

As shown in FIG. 12, the medical instrument 4 may be placed into the instrument bag 6. In some embodiments, the used or contaminated medical instrument 4 may be placed into the instrument bag 6 after medical use. The subjacent label adhesive cover 15 may be removed from the subjacent label 10. Removing the subjacent label adhesive cover 15 may expose the second adhesive 13, where the second adhesive 13 may be disposed on the exterior surface 7 of the instrument bag 6. Adhering the second portion 14 of the subjacent label 10 to the instrument bag 6 may close and seal the opening 8 of the instrument bag 6. This may seal the contaminated medical instrument 4 for safe transport.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description. Future-filed applications claiming priority to this application may claim the disclosed subject matter in a different manner and generally may include any set of one or more limitations as variously disclosed or otherwise demonstrated herein.

The invention claimed is:

1. A system, comprising:
   an instrument bag configured to receive a medical instrument, wherein the instrument bag forms an opening;
   a subjacent label at least partially disposed along a peripheral surface of the opening of the instrument bag, the subjacent label including:
      a first portion engaged to an exterior surface of the instrument bag; and
      a second portion configured to be removably engaged to the instrument bag; and
   a superjacent label at least partially disposed along the peripheral surface of the opening of the instrument bag, the superjacent label including:
      an attached portion removably adhered to at least one of the subjacent label and the exterior surface of the instrument bag; and
      a free portion configured to be removably engaged to the instrument bag.

2. The system of claim 1, wherein the free portion of the superjacent label comprises a removable adhesive cover configured to expose an adhesive when the removable adhesive cover is removed.

3. The system of claim 2, wherein the free portion of the superjacent label is adhered to an opposing side of the instrument bag to close the opening of the instrument bag.

4. The system of claim 2, wherein the removable adhesive cover is substantially L-shaped.

5. The system of claim 3, wherein the superjacent label is removed from the subjacent label and the instrument bag.

6. The system of claim 1, wherein the second portion of the subjacent label comprises a subjacent label adhesive cover configured to expose a second adhesive when the subjacent label adhesive cover is removed.

7. The system of claim 6, wherein the second portion of the subjacent label is adhered to an opposing side of the instrument bag to close the opening of the instrument bag.

8. The system of claim 1, wherein the superjacent label is disposed over the subjacent label.

9. The system of claim 1, wherein a length of the superjacent label is greater than a length of the subjacent label.

10. The system of claim 3, wherein the superjacent label forms a pocket between the attached portion and the free portion.

11. The system of claim 10, further comprising a data carrier disposed within the pocket.

12. The system of claim 11, wherein the data carrier comprises a disinfectant material and includes information relating to the medical instrument.

13. The system of claim 1, wherein the superjacent label indicates that the medical instrument is clean, and the subjacent label indicates that the medical instrument is contaminated.

14. The system of claim 1, further comprising an outer bag, wherein the instrument bag is disposed within the outer bag.

15. The system of claim 1, further comprising a box, wherein one or more instrument bags are disposed within the box for sterile transport.

16. The system of claim 1, wherein the instrument bag includes a fluid-impervious material and is configured to be sealed to prevent ingress of contaminants.

17. A method, comprising:
   disposing a subjacent label at least partially along a peripheral surface of an opening of an instrument bag, wherein the subjacent label includes:
      a first portion engaged to an exterior surface of the instrument bag; and
      a second portion configured to be removably engaged to the instrument bag; and
   disposing a superjacent label at least partially along the peripheral surface of the opening of the instrument bag, wherein the superjacent label includes:
      an attached portion removably adhered to at least one of the subjacent label and the exterior surface of the instrument bag; and
      a free portion configured to be removably engaged to the instrument bag.

18. The method of claim 17, further comprising:
   removing a removable adhesive cover disposed on the free portion of the superjacent label to expose an adhesive; and adhering the free portion of the superjacent label to an opposing side of the instrument bag to close the opening of the instrument bag.

19. The method of claim 17, further comprising removing the attached portion of the superjacent label from at least one of the subjacent label and the exterior surface of the instrument bag.

20. The method of claim 17, further comprising:
removing a subjacent label removable adhesive cover disposed on the second portion of the subjacent label to expose a second adhesive; and
adhering the second portion of the subjacent label to the opposing side of the instrument bag to close the opening of the instrument bag.

\* \* \* \* \*